United States Patent

Galliani et al.

[11] Patent Number: 4,990,531
[45] Date of Patent: Feb. 5, 1991

[54] DERIVATIVES OF 1-ARYLSULPHONYL-2-PYRROLIDINONE AND THEIR USE AS MEDICAMENTS

[75] Inventors: Giulio Galliani; Fernando Barzaghi, both of Monza, Italy; Michel Fortin, Paris, France; Carlo Gorini; Emilio Toja, both of Milan, Italy

[73] Assignee: Roussel Uclaf, Paris, France

[21] Appl. No.: 315,170

[22] Filed: Feb. 24, 1989

[30] Foreign Application Priority Data

Feb. 26, 1988 [IT] Italy ............... 19560 A/88

[51] Int. Cl.$^5$ .......... A61K 31/40; C07D 207/48
[52] U.S. Cl. .......... 514/425; 540/602; 544/141; 544/372; 546/208; 548/523; 548/542
[58] Field of Search ........ 548/542, 523; 514/424, 514/425

[56] References Cited

U.S. PATENT DOCUMENTS 4,217,130 8/1980 Tsuruta et al. ............... 548/542
4,833,156 5/1989 Sakakibara et al. ........... 514/424

FOREIGN PATENT DOCUMENTS 215624 8/1988 Japan.

OTHER PUBLICATIONS

Chem. Abstract 110:75307d (1989), Sakakibara et al.

*Primary Examiner*—Mukund J. Shah
*Assistant Examiner*—Philip Datlow
*Attorney, Agent, or Firm*—Stevens, Davis, Miller & Mosher

[57] ABSTRACT

Compounds useful for the treatment of patients suffering from muscle spasms of the formula (I)

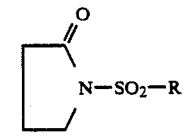

in which R represents the radical

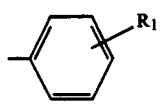

in which $R_1$, in any position on the phenyl nucleus, represents a linear, branched or cyclic alkyl, alkenyl or alkynyl, containing up to 8 carbon atoms, or the radical

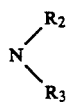

in which $R_2$ and $R_3$, identical or different each represents a hydrogen atom, a linear alkyl, alkenyl or alkynyl, containing up to 8 carbon atoms, or form together with the nitrogen atom to which they are joined, a heterocyclic radical optionally containing another heteroatom, or $NO_2$, or $OR'$, $R'$ representing hydrogen, a linear, branched or cyclic alkyl containing up to 8 carbon atoms, or aryl containing up to 14 carbon atoms, or an $SR_4$ or $S(O)R_5$ radical, $R_4$ and $R_5$ representing a linear, branched or cyclic alkyl, alkenyl or alkynyl, containing up to 8 carbon atoms, or R represents naphthyl, optionally substituted by an $R_1$ radical, as defined above; also therapeutic compositions containing the same and method of use.

4 Claims, No Drawings

DERIVATIVES OF 1-ARYLSULPHONYL-2-PYRROLIDINONE AND THEIR USE AS MEDICAMENTS

The present invention relates to new derivatives of 1-arylsulphonyl-2-pyrrolidinone, their preparation process, intermediates thereof, their use as medicaments and the compositions containing them.

A subject of the invention is compounds of formula (I):

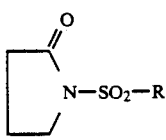
(I)

in which R represents the radical

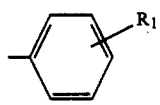

in which $R_1$, in any position on the phenyl nucleus, represents a linear, branched or cyclic alkyl, alkenyl or alkynyl, containing up to 8 carbon atoms, or the radical $$N\begin{matrix}R_2\\R_3\end{matrix}$$

in which $R_2$ and $R_3$, identical or different each represents a hydrogen atom, a linear alkyl, alkenyl or alkynyl, containing up to 8 carbon atoms, or form together with the nitrogen atom to which they are joined, a heterocyclic radical optionally containing another heteroatom, or $NO_2$, or $OR'$, $R'$ representing hydrogen, a linear, branched or cyclic alkyl containing up to 8 carbon atoms, or aryl containing up to 14 carbon atoms, or an $SR_4$ or $S(O)R_5$ radical, $R_4$ and $R_5$ representing a linear, branched or cyclic alkyl, alkenyl or alkynyl, containing up to 8 carbon atoms, or R represents naphthyl, optionally substituted by an $R_1$ radical, as defined above.

As alkyl there is preferred an alkyl containing from 1 to 5 carbon atoms, for example, one of the following: methyl, ethyl, n-propyl, isopropyl, n-butyl, isobutyl, tert-butyl, n-pentyl, n-hexyl, cyclopropyl, cyclobutyl, cyclopentyl or cyclohexyl.

As alkenyl there is preferred ethenyl, propenyl and butenyl. When $R_2$ and $R_3$ form together with the nitrogen atom to which they are joined, a heterocyclic radical optionally containing another heteroatom, there is preferred piperidyl, piperazinyl, morpholinyl or pyrrolidinyl.

As aryl there is preferred phenyl or naphthyl.

Among the preferred compounds of the invention, there can be cited compounds of formula (I) in which R represents the radical

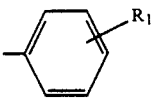

$R_1$ having the same significance as above, and in particular those in which the radical $R_1$ is in position 4. There can also be cited compounds of formula (I) in which $R_1$ represents a linear or branched alkyl containing up to 8 carbon atoms and in particular tert-butyl or also those in which $R_1$ represents the radical

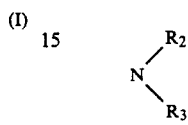

in which $R_2$ and $R_3$ represent linear or branched alkyl containing up to 8 carbon atoms or form together with the nitrogen atom to which they are joined, a heterocyclic radical, or also those in which $R_1$ represents $SR_4$, $R_4$ representing a linear or branched alkyl containing up to 4 carbon atoms and in particular methyl.

Among the preferred compounds of the invention, there can be cited the compounds, the preparation of which is given hereafter in the Examples, and quite particularly the compounds of Examples 1, 2, 3, 4 and 10.

The compounds of formula (I) show useful pharmacological properties and in particular a specific and selective antimuscarine activity.

A subject of the invention is therefore the products of formula (I) as medicaments, useful in particular for the antispasmodic treatment of muscle spasms in gastroenterology, in gynaecology, in obstetrics, in urology, in hepatology and in radiology.

A subject of the invention is more particularly, as medicaments, the products of Examples 1, 2, 3, 4 and 10.

The usual posology is variable according to the affection in question, the patient treated and the administration route; it can be between 10 mg and 1 g per day, and preferably between 20 mg and 100 mg per day, and more particularly between 30 and 60 mg per day in one or more doses, for the product of Example 1, administered by oral route.

A subject of the present invention is also pharmaceutical compositions containing as active principle at least one product of formula (I). The pharmaceutical compositions of the invention can be solid or liquid and can be presented in the pharmaceutical forms currently used in human medicine, such as for example plain or sugar-coated tablets, gelules, granules, suppositories and injectable preparations; they are prepared according to the usual methods.

The active principle or principles can be incorporated in the excipients usually employed in these pharmaceutical compositions, such as talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents, and preservatives.

A subject of the invention is also a preparation process for compounds of formula (I) characterized in that 2-pyrrolidinone

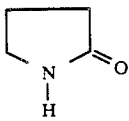

is submitted to the action of a compound of formula (II):

R-SO₂Hal     (II)

in which Hal represents chlorine or bromine, and R has the same significance as above, so as to obtain the corresponding compound of formula (I).

In a preferred method of carrying out the invention process, the reaction between 2-pyrrolidinone and the product of formula (II) is carried out:

(a) in the presence of a strong base such as butyllithium, an alkali hydride such as sodium hydride or sodium bis(trimethylsilyl) amide;

(b) in a solvent chosen from the group constituted by tetrahydrofuran , benzene , dimethylformamide, dimethylsulphoxide, monoethyl ether of diethylene glycol, or diethyl ether of diethylene glycol.

A subject of the invention is also a preparation process for compounds of formula (I), characterized in that 4-amino butyric acid is submitted to the action of a compound of formula (II):

R-SO₂-Hal     (II)

in which R and Hal have the significance indicated previously so as to obtain a compound of formula (III):

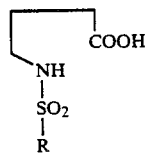

in which R has the significance already indicated, which is cyclized so as to obtain the corresponding product of formula (I).

In a preferred method of carrying out the process described above:

the reaction of the 4-amino butyric acid with the compound of formula (II) is carried out in the presence of a mineral base such as sodium- or potassium-hydroxide in an organic solvent such as tetrahydrofuran;

the cyclization of the compound of formula (III) is carried out in the presence of a dehydration agent such as acetic anhydride, phosphoric anhydride, phosphoric acid or hexamethyldisilazane.

A subject of the invention is also the products of formula (III), as defined previously, as new industrial products.

The following examples illustrate the invention without however limiting it.

EXAMPLE 1:

1-(4-tert-butyl benzenesulphonyl)-2-pyrrolidinone 1.65 g of 2-pyrrolidinone in solution in 75 cm³ of tetrahydrofuran is cooled to −5° C., and 12.1 cm³ of a 1.6M solution of n-butyllithium in hexane is added, maintaining the temperature between −5° C. and 0° C. Agitation is carried out for 25 minutes at −5° C.; the mixture is cooled to −20° C. and 4.5 g of 4-tert-butylphenylsulphonyl chloride is added [Recueil Trav. Chim. Pays-Bas, 53, 1101 (1934)]. After allowing to return to ambient temperature, the tetrahydrofuran is evaporated off under reduced pressure, the residue is taken up with water, filtered and crystallized from ethanol. 2.75 g of expected product is obtained.

m.p.=131°–133° C.

| Analysis: C₁₄H₁₉NO₃S: 281.376 | | | | | | |
|---|---|---|---|---|---|---|
| Calculated: | C % | 59.76 | H % | 6.81 | N % | 4.98 |
| Found: | | 59.62 | | 6.78 | | 4.79 |

EXAMPLE 2:

1-[4-(diethylamino)benzenesulphonyl]-2-pyrrolidinone 0.69 g of 2-pyrrolidinone in solution in 25 cm³ of tetrahydrofuran is cooled to −10° C., and 4.89 cm³ of a 1.6M solution of N-butyllithium in n-hexane is added, operating at a temperature lower than 5° C. After agitation for 20 minutes, the mixture is cooled to −25° C., and drop by drop poured into a solution of 2 g of diethylaminobenzenesulphonyl chloride in 15 cm³ of tetrahydrofuran, maintaining the temperature lower than −20° C. The whole is left to return to ambient temperature and agitated for 2 hours. The solvent is eliminated under reduced pressure and the residue is chromatographed on silica (eluent: ethyl acetate-n-hexane 1-1). The residue is taken up in isopropyl ether and 0.74 g of expected product is obtained.

m.p.=128°–130° C.

| Analysis: C₁₄H₂₀N₂O₃S: 296.392 | | | | | | |
|---|---|---|---|---|---|---|
| Calculated: | C % | 56.73 | H % | 6.8 | N % | 9.45 |
| Found: | | 56.59 | | 6.73 | | 9.38 |

The 4-(diethylamino)-benzenesulphonyl chloride used at the start of the example was prepared as follows:

24.84 g of 4-diethylaminobenzenesulphonic acid [Liebigs Ann. Chem. (1982) 282]and 22.56 g of phosphorus pentachloride are mixed together in 350 cm³ of methylene chloride and heated to reflux for 4 hours. The mixture is cooled to ambient temperature, the solvent is evaporated off under reduced pressure, the residue is taken up with toluene, filtered on celite and concentrated to dryness under reduced pressure. 20.39 g of expected product is obtained.

EXAMPLE 3:

1-[4-(dimethylamino)benzenesulphonyl-2-pyrrolidinone 3.44 g of sodium hydride (at 55–60% in oil) is added to a solution comprising 6.11 g of 2-pyrrolidinone and 200 cm³ of dioxan, with agitation for one hour at ambient temperature. 15.76 cm³ of 4-dimethylaminobenzenesulphonyl chloride [Beritche 43, 3038 (1910)]in solution in 250 cm³ of dioxan is added drop by drop, with agitation for one hour at ambient temperature. The sodium chloride is filtered off on celite, the dioxan is evaporated off under reduced pressure, the residue is crystallized from acetone and 3.90 g of expected product is obtained.

m.p.=202°–204° C.

| Analysis: $C_{12}H_{16}N_2O_3S$: 268.340 | | | | | | |
|---|---|---|---|---|---|---|
| Calculated: | C % | 53.71 | H % | 6.01 | N % | 10.44 |
| Found: | | 53.92 | | 5.97 | | 10.50 |

(Soluble in chloroform; slightly soluble in acetone, benzene and alcohol at 95°; insoluble in ethyl ether, water, 2N hydrochloric acid and 2N sodium hydroxide.)

EXAMPLE 4:

1[-4-(methylthio)benzenesulphonyl]-2-pyrrolidinone 16.95 cm³ of a 1.6M solution of n-butyllithium in n-hexane is added drop by drop to 2.29 g of 2-pyrrolidinone in solution in 160 cm³ of anhydrous tetrahydrofuran cooled to -30° C., maintaining the temperature at -30° C. After agitation for 30 minutes, the mixture is poured drop by drop into a solution containing 6 g of 4-methylthio-benzenesulphonyl chloride [J. Chem. Soc. (1948) 604]in 10 cm³ of tetrahydrofuran, operating between -30° and -25° C. The whole is left to return to ambient temperature. The solvent is evaporated off under reduced pressure, the residue is taken up in water and the solid is filtered off. After crystallization from isopropanol, 3.80 g of expected product is obtained
m.p.=123°-125° C.

| Analysis: $C_{11}H_{13}NO_3S_2$: 271.36 | | | | | | |
|---|---|---|---|---|---|---|
| Calculated: | C % | 48.69 | H % | 4.83 | N % | 5.16 |
| Found: | | 48.91 | | 4.69 | | 5.22 |

EXAMPLE 5:

1-(4 isopropyloxybenzenesulphonyl)-2-pyrrolidinone 9.6 cm³ of a 1.6M solution of n-butyllithium in hexane is added to 1.3 g of 2-pyrrolidinone in solution in 90 cm³ of tetrahydrofuran, cooled to -30° C., maintaining the temperature between -20° C. and -30° C. After agitation for one hour at -30° C., at this temperature 4 g of 4-isopropyloxybenzenesulphonyl [Helv. Chim. Acta 39, 1579 (1956)]in solution in 6 cm³ of tetrahydrofuran is poured drop by drop into the mixture. After agitation for one hour at -30° C., the whole is left to return to ambient temperature. The solvent is evaporated off under reduced pressure and the residue is chromatographed on silica (eluent: cyclohexane-ethyl acetate 7-3). After crystallization from isopropanol, 1.5 g of expected product is obtained.
m.p.=88°-90° C.

| Analysis: $C_{13}H_{17}NO_4S$: 283.35 | | | | | | |
|---|---|---|---|---|---|---|
| Calculated: | C % | 55.10 | H % | 6.05 | N % | 4.94 |
| Found: | | 55.07 | | 5.98 | | 4.90 |

EXAMPLE 6:

1[4-(methylsulphinyl)benzenesulphonyl]-2-pyrrolidinone

A solution containing 2.41 g of m-chloroperbenzoic acid in 48 cm³ of methylene chloride is added to 3.4 g of 1-(4-methylthiobenzene-sulphonyl)pyrrolidin-2-one prepared as in Example 4 in solution in 34 cm³ of methylene chloride, at a temperature not exceeding 25° C. After agitation at ambient temperature for 30 minutes, the reaction medium is then treated with a 10% aqueous solution of sodium sulphite. The organic phase is separated off, washed with a 5% aqueous solution of sodium bicarbonate, then with water. After drying, the solvent is evaporated off under reduced pressure, and the residue is crystallized from 95% ethanol. 1.70 g of expected product is obtained.
m.p.=127°-129° C.

| Analysis: $C_{11}H_{13}NO_4S_2$: 287.36 | | | | | | |
|---|---|---|---|---|---|---|
| Calculated: | C % | 45.98 | H % | 4.56 | N % | 4.87 |
| Found: | | 45.87 | | 4.60 | | 4.81 |

EXAMPLE 7:

1-(3-methoxybenzenesulphonyl)-2-pyrrolidinone 15.75 cm³ of a 1.6M solution of N-butyllithium in hexane is added to 2.22 g of 2-pyrrolidinone in solution in 80 cm³ of tetrahydrofuran and cooled to -25° C., the temperature being maintained between -25° C. and -20° C. After agitation for 30 minutes at -25° C., a solution of 5.40 g of 3-methoxybenzene sulphonyl chloride [J. Chem. Soc. P.T.2., 579 (1982)]in 40 cm³ of tetrahydrofuran is poured drop by drop into the mixture, operating between -25° C. and -20° C. After agitation for 30 minutes at -25° C., the whole is allowed to return to ambient temperature. The solvent is evaporated under reduced pressure; the residue is taken up in water, filtered and crystallized from isopropanol. 3.5 g of expected product is obtained
m.p.=108°-109° C.

| Analysis: $C_{11}H_{13}NO_4S$: 255.298 | | | | | | |
|---|---|---|---|---|---|---|
| Calculated: | C % | 51.75 | H % | 5.13 | N % | 5.49 |
| Found: | | 51.84 | | 5.12 | | 5.54 |

EXAMPLE 8:

1-(2-naphthylsulphonyl)-2-pyrrolidinone 15.6 cm³ of a 1.6M solution of butyllithium in hexane is added to 2.13 g of 2-pyrrolidinone in solution in 80 cm³ of tetrahydrofuran, cooled to -10° C., maintaining the temperature between -5° C. and +5° C. After agitation at -5° C. for 25 minutes, 6.12 g of beta-naphthalene-sulphonyl chloride is added, without exceeding 0° C. The whole is then left to return to ambient temperature. The solvent is evaporated off under reduced pressure, the residue is taken up in ethyl acetate, and the lithium chloride is filtered off and after evaporating under reduced pressure, the residue is taken up in water and filtered. Finally after crystallization from isopropanol, 4 g of expected product is obtained.
m.p.=118°-120° C.

| Analysis: $C_{14}H_{13}NO_3S$: 275.3 | | | | | | |
|---|---|---|---|---|---|---|
| Calculated: | C % | 61.07 | H % | 4.76 | N % | 5.09 |
| Found: | | 60.91 | | 4.72 | | 4.99 |

EXAMPLE 9:

1-(4-pyrrolidinyl)phenylsulphonyl]-2-pyrrolidinone

Stage A:
4-(4-pyrrolidinylphenylsulphonylamino)butyric acid 4.9 g of 4-pyrrolidinebenzenesulphonyl chloride (Chem. Abst. 46, 8647 F), is added to a solution comprising 2.06 g of 4-aminobutyric acid and 2.4 g of sodium hydroxide in 40 cm$^3$ of water, then 50 cm$^3$ of tetrahydrofuran is added in order to obtain a perfect solution. After agitation for 24 hours at ambient temperature, followed by acidifying with acetic acid, the solvent is evaporated off at ambient temperature. After extraction with chloroform, the organic phase is dried on sodium sulphate, filtered and evaporated to dryness. 2.4 g of expected product is obtained.
m.p.=161°–163° C.

| Analysis: $C_{14}H_{20}N_2O_4S$: 312.39 | | | | | | |
|---|---|---|---|---|---|---|
| Calculated: | C % | 53.83 | H % | 6.45 | N % | 8.97 |
| Found: | | 53.16 | | 6.25 | | 8.72 |

Stage B:
1-[(4-pyrrolidinyl)phenylsulphonyl]-2-pyrrolidinone.

2.5 g of product prepared as in stage A and 2.5 g of sodium acetate are heated for 4 hours at reflux in 50 cm$^3$ of acetic anhydride, followed by cooling and evaporating to dryness. The residue is taken up in 150 cm$^3$ of benzene, heated to reflux and filtered on active charcoal. By addition of n-hexane, a precipitate is obtained which is filtered off and washed with hexane. 1.7 g of expected product is obtained.
m.p.=235°–237° C.

| Analysis: $C_{14}H_{18}N_2O_3S$: 294.38 | | | | | | |
|---|---|---|---|---|---|---|
| Calculated: | C % | 57.12 | H % | 6.16 | N % | 9.51 |
| Found: | | 56.77 | | 6.24 | | 9.31 |

EXAMPLE 10:

1-[4-(1-piperidinyl)phenylsulphonyl]-2-pyrrolidinone

Stage A: 4-(4-piperidinephenylsulphonylamino)butyric acid.

1 g of 4-piperidinebenzenesulphonyl chloride is added to a solution comprising 0.39 g of 4-aminobutyric acid, 0.462 g of sodium hydroxide in solution in 10 cm$^3$ of water, then 5 cm$^3$ of tetrahydrofuran is added so as to obtain a solution. The solution is agitated for 24 hours at ambient temperature, then acidified with acetic acid. The solvent is evaporated off, the organic phase is extracted with chloroform, dried on sodium sulphate, filtered and evaporated to dryness. After crystallization from ethyl acetate, 0.5 g of expected product is obtained.
m.p.=130°–132° C.

| Analysis: $C_{15}H_{22}N_2O_4S$: 326.43 | | | | | | |
|---|---|---|---|---|---|---|
| Calculated: | C % | 55.19 | H % | 6.79 | N % | 8.58 |
| Found: | | 54.69 | | 6.72 | | 8.37 |

Stage B:
1-[4-(1-piperidinyl)phenylsulphonyl]-2-pyrrolidinone.

A mixture made up of 3 g of product obtained as in stage A and 3 g of sodium acetate in 60 cm$^3$ of acetic anhydride is taken to reflux for 3 hours, then cooled to ambient temperature and evaporated to dryness. After extraction with chloroform and with water, the organic phase is separated, dried on sodium sulphate, filtered and evaporated. 2.5 g of expected product is obtained.
m.p.=168°–170° C.

After crystallization from isopropanol, 1.80 g of product is obtained.
m.p.=170°–172° C.

| Analysis: $C_{15}H_{20}N_2O_3S$: 308.41 | | | | | | |
|---|---|---|---|---|---|---|
| Calculated: | C % | 58.42 | H % | 6.54 | N % | 9.08 |
| Found: | | 58.31 | | 6.46 | | 8.89 |

The 4-piperidinebenzenesulphonyl chloride used at the start of Example 10 was prepared as follows.

9.3 g of dioxan is added to a solution comprising 8.46 g of sulphuric anhydride in 45 cm$^3$ of methylene chloride, cooled to 0°C./+5° C., then, at the same temperature, 17.1 g of N-phenylpiperidine in solution in 45 cm$^3$ of methylene chloride is added. The mixture is left to return to ambient temperature, then heated to reflux for one hour. After evaporation to dryness, the residue is taken up by a 10% solution of sodium carbonate. The aqueous phase is washed with benzene and concentrated; the residue is dried and treated with 200 cm$^3$ of phosphorus oxychloride and 21.8 g of phosphorus pentachloride for 12 hours at ambient temperature. After evaporation to dryness, the residue is taken up with chloroform and water, the organic phase is separated, dried on sodium sulphate, filtered and evaporated to dryness. 19 g of product is obtained which is used just as it is.

EXAMPLE 11:

1-(4-morpholino)phenylsulphonyl]-2-pyrrolidinone

Stage A: (4-morpholinophenylsulphonylamino)butyric acid.

10 g of 4-morpholinobenzenesulphonyl chloride is added to a solution comprising 3.94 g of 4-amino butyric acid and 4.6 g of sodium hydroxide in 80 cm$^3$ of water, then 70 cm$^3$ of tetrahydrofuran is added so as to obtian a solution. The temperature increases from 20° to 27° C. The solution is allowed to return to ambient temperature and maintained under agitation for 24 hours, after which it is acidified with acetic acid, and the solvent is evaporated under reduced pressure. The residue is taken up with 50 cm$^3$ of distilled water; the precipitate is filtered off, washed with water, dried and 7.6 g of expected product is obtained, m.p.=163°–165° C., which is recrystallized from ethyl acetate.
m.p.=167°–168° C.

| Analysis: $C_{14}H_{20}N_2O_5S$: 328.39 | | | | | | |
|---|---|---|---|---|---|---|
| Calculated: | C % | 51.20 | H % | 6.14 | N % | 8.53 |
| Found: | | 51.21 | | 6.07 | | 8.61 |

Stage B:

1-[(4-morpholino-phenylsulphonyl]-2-pyrrolidinone.

6.2 g of product obtained in Stage A, 6.2 g of sodium acetate and 124 cm³ of acetic anhydride are heated to reflux for 4 hours. After cooling to ambient temperature and evaporating to dryness, the residue is taken up with 50 cm³ of water, filtered, washed with 10 cm³ of water and dried. 5.65 g of expected product is obtained.

m.p.=208°–210° C. After recrystallization from acetone, 4.3 g of product is obtained, melting at 210°–211° C.

| Analysis: $C_{14}H_{18}N_2O_4S$: 310.28 | | | | | | |
|---|---|---|---|---|---|---|
| Calculated: | C % | 54.17 | H % | 5.85 | N % | 9.03 |
| Found: | | 54.30 | | 5.91 | | 8.92 |

The 4-morpholinobenzenesulphonyl chloride used at the start of Example 11 was prepared as follows.

9.68 g of dioxane, then 17.95 g of N-phenylmorpholine dissolved in 30 cm³ of methylene chloride are added drop by drop to a solution comprising 8.8 g of sulphuric anhydride in 100 cm³ of methylene chloride cooled to between −5° C. and +3° C., without the temperature exceeding +5° C. The whole is left to return to ambient temperature, then heated to reflux for one hour and a half. After cooling to ambient temperature, and extracting with water, the aqueous phase is neutralized with sodium carbonate, evaporated to dryness and the residue is dried under reduced pressure at 90° C. for 4 hours. 19.5 g of sodium salt is obtained which is treated with 21 g of phosphorus pentachloride in 100 cm³ of methylene chloride, heating to reflux for 4 hours. After cooling to ambient temperature and evaporating to dryness, the residue is taken up in benzene with a little water. The organic phase is separated, dried on sodium sulphate, filtered and the solvent is evaporated off. 11.5 g of expected product is obtained. m.p. 105°–108° C. After crystallization from benzene, the product is obtained, melting at 120°–122° C.

| Analysis: $C_{10}H_{12}ClNO_3S$: 261.77 | | | | | | |
|---|---|---|---|---|---|---|
| Calculated: | C % | 45.88 | H % | 4.62 | N % | 5.35 |
| Found: | | 45.67 | | 4.59 | | 5.44 |

EXAMPLE 12:

1-[(4-cyclopentyl)phenylsulphonyl]-2-pyrrolidinone 8 cm³ of a 1.5M solution of n-butyllithium in n-hexane is poured into a solution comprising 1.02 g, or 0.9 cm³ of 2-pyrrolidinone in 50 cm³ of tetrahydrofuran, cooled to −70° C. without the temperature exceeding −60° C. After 15 minutes, 3 g of benzenesulphonyl-4-cyclopentyl chloride in solution in 12 cm³ of tetrahydrofuran is added, maintaining the temperature between −65° and −70° C. After allowing to return to ambient temperature over 2 hours and evaporating to dryness, the residue is chromatographed on silica (eluent: ethyl acetate-n-hexane 1-3) and 2.6 g of expected product is obtained.

m.p.=105°–106° C., which after crystallization from isopropanol gives 2 g of product melting at 105°–106° C.

| Analysis: $C_{15}H_{19}NO_3S$: 293.40 | | | | | | |
|---|---|---|---|---|---|---|
| Calculated | C % | 61.41 | H % | 6.53 | N % | 4.77 |
| Found | | 61.22 | | 6.71 | | 5.06 |

The benzenesulphonyl-4-cyclopentyl chloride used at the start of Example 12 was prepared as follows.

14.7 g, or 12 cm³, of trimethylsilyl chlorosulphonate is added to 11.5 g of phenylcyclopentane [Chem. Abstr. 51, 7317c (1957)], at between +5° C. and +10° C. The mixture is allowed to return to ambient temperature and agitated for 2 hours. After evpaoration to dryness, the residue is dissolved in 100 cm³ of chloroform, treated with 7.5 g of phosphorus pentachloride and heated for 2 hours at reflux. After evaporating to dryness, the oily residue is chromatographed on silica (eluent: ethyl acetate-n-hexane 1-3) and 3.3 g of expected product is obtained.

m.p.=48°–50° C.

EXAMPLE 13:

1-(4-cyclohexyl)phenylsulphonyl]-2-pyrrolidinone

The operation is carried out as in Example 12, using 1.97 g of 2-pyrrolidinone in 100 cm³ of tetrahydrofuran, 15.5 cm³ of a 1.5M solution of n-butyllithium in hexane, and 6 g of (4-cyclohexyl)benzene-sulphonyl chloride [J. Am. Chem. Soc. 62, 513 (1940)]in 24 cm³ of tetrahydrofuran. 3 g of expected product is obtained.

m.p.=91°–92° C. After crystallization from isopropanol, 2 g of product is obtained.

m.p.=91°–92° C.

| Analysis: $C_{16}N_{21}NO_3S$: 307.42 | | | | | | |
|---|---|---|---|---|---|---|
| Calculated | C % | 62.51 | H % | 6.88 | N % | 4.56 |
| Found | | 62.29 | | 6.74 | | 4.69 |

EXAMPLE 14:

1(4-dipropylamine)phenylsulphonyl-2-pyrrolidinone

The operation is carried out as in Example 12, using 1.39 g of 2-pyrrolidinone in 42 cm³ of tetrahydrofuran, 10.8 cm³ of a 1.5M solution of n-butyllithium in n-hexane, then at between −20° C. and −10° C., 4.5 g of (4-dipropylamino)benzenesulphonyl in 25 cm³ of tetrahydrofuran is added. 2 g of expected product is obtained.

m.p.=88°–90° C. After crystallization from isopropanol, 1.5 g of product is obtained, melting at 92°–93° C.

| Analysis: $C_{16}H_{24}N_2O_3S$: 324.454 | | | | | | |
|---|---|---|---|---|---|---|
| Calculated | C % | 59.23 | H % | 7.46 | N % | 8.63 |
| Found | | 59.13 | | 7.53 | | 8.44 |

The (4-dipropylamino)benzenesulphonyl chloride used at the start of Example 14 was prepared as follows:

10.2 g of (N,N-dipropylaniline) (Annalen der Chemie 214, 168) is added to a solution cooled to +5° C./+10° C. comprising 10.86 g (or 8.86 cm³) of trimethylsilyl chlorosulphonate and 50 cm³ of methylene chloride. The mixture is allowed to return to ambient temperature and evaporated to dryness. The residue is taken up in acetone, filtered and dried and 4.9 g of acid is obtained, to which is added 100 cm³ of methylene chloride and 2.63 g of phosphorus pentachloride, heating to reflux for 4 hours. After cooling to ambient temperature and evaporating to dryness, the oily residue is taken up with benzene and water. The organic phase is separated, dried on sodium sulphate, filtered and evaporated to dryness. 4.5 g of expected product is obtained which is used just as it is.

EXAMPLE 15:

1[(4-dibutylamino)phenylsulphonyl]-2-pyrrolidinone

The operation is carried out as in Example 12, using 1.76 g of 2-pyrrolidinone in 51 cm$^3$ of tetrahydrofuran, 13.8 cm$^3$ of a 1.5M solution of n-butyllithium in n-hexane at a temperature between −20° C. and −15° C., then 6.3 g of 4-dibutylaminobenzenesulphonyl chloride in 35 cm$^3$ of tetrahydrofuran is added. After chromatography on silica (eluent: ethylacetate-n-hexane 1-1) and crystallization from isopropanol, 3 g of expected product is obtained.

m.p.=73°-74° C.

| Analysis: $C_{18}H_{28}N_2O_3S$: 352.51 | | | | | | |
|---|---|---|---|---|---|---|
| Calculated | C % | 61.33 | H % | 8.01 | N % | 7.95 |
| Found | | 61.14 | | 8.03 | | 7.86 |

The 4-dibutylaminobenzenesulphonyl chloride used at the start of Example 15 was prepared as follows.

The operation is carried out as indicated for the preparation of the starting product of Example 14, using 10 g of (N,N-dibutylaniline) [J. Chem. Soc. (1956), 3293], and 9.19 g (or 7.5 cm$^3$) of trimethysilyl chlorosulphonate in 50 cm$^3$ of methylene chloride. After evaporation to dryness, the residue is taken up in 100 cm$^3$ of methylene chloride, then 10.1 g of phosphorus pentachloride is added, heating to reflux for an hour and a half. After cooling and evaporation to dryness, the residue is taken up in water and extracted with chloroform. The extracts are dried on sodium sulphate, filtered, and evaporated to dryness. The residue is chromatographed on silica (eluent: ethyl acetate-n-hexane 1-1) and 6.3 g of expected product is obtained which is used just as it is.

EXAMPLE 16:

1-[(4-diisopropylamino)phenylsulphonyl]-2-pyrrolidinone

The operation is carried out as in Example 12 using 2.76 g of 2-pyrrolidinone in 81 cm$^3$ of tetrahydrofuran, 21.7 cm$^3$ of a 1.5M solution of n-butyllithium in n-hexane at a temperature between −20° C. and −15° C., then 9 g of (4-diisopropylamino)benzenesulphonyl chloride in 45 cm$^3$ of tetrahydrofuran. After chromatography (eluent: ethyl acetate-n-hexane 1-2), 3.4 g of expected product is obtained.

m.p.=140°-145° C., then 142°-145° C. after crystallization from isopropanol.

| Analysis: $C_{16}H_{24}N_2O_3$: 324.45 | | | | | | |
|---|---|---|---|---|---|---|
| Calculated: | C % | 59.23 | H % | 7.46 | N % | 8.63 |
| Found | | 59.09 | | 7.38 | | 8.57 |

The 4-diisopropylaminobenzenesulphonyl chloride used at the start of Example 16 was prepared as follows.

The operation is carried out as indicated for the preparation of the starting product of Example 14, using 13 g of (N,N-diisopropyl-aniline) [J. Org. Chem. 22, 832 (1957)], and 14 g (or 11.43 cm$^3$) of trimethylsilyl chlorosulphonate in 50 cm$^3$ of methylene chloride. After evaporation to dryness, the residue is taken up in 100 cm$^3$ of methylene chloride, 14 g of phosphorus pentachloride is added and the whole is taken to boiling point for 4 hours. After evaporation to dryness, the residue is taken up in 50 cm$^3$ of water, and extraction is carried out with ether. The extracts are dried on sodium sulphate, filtered and evaporated. 9.6 g of expected product is obtained, which is used just as it is.

EXAMPLE 17:

1-(4-isopropylthiophenylsulphonyl)-2-pyrrolidinone

The operation is carried out as in Example 12, using 1.7 g of 2-pyrrolidinone in 61 cm$^3$ of tetrahydrofuran, 13.3 cm$^3$ of a 1.5M solution of n-butyllithium in n-hexane and 5 g of 4-isopropylsulphidebenzenesulphonyl chloride in 5 cm$^3$ of tetrahydrofuran. The mixture is left to return to ambient temperature and evaporated to dryness. The residue is taken up in water, and the precipitate is filtered and dried. 3.1 g of expected product is obtained.

m.p.=62°-66° C., which is recrystallized from isopropanol, and 2.4 g of product is recovered, melting at 68°-70° C.

| Analysis: $C_{13}H_{17}NO_3S_2$ | | | | | | |
|---|---|---|---|---|---|---|
| Calculated | C % | 52.15 | H % | 5.72 | N % | 4.68 |
| Found | | 51.86 | | 5.63 | | 4.57 |

The 4-isopropylsulphidebenzenesulphonyl chloride used at the start of Example 17 was prepared as follows.

5.8 g of dioxan is added drop by drop, at a temperature between −5° C. and +3° C., to a solution comprising 5.32 g of sulphuric anhydride (Coll. Org. Synth. IV, p. 846) in 24 cm$^3$ of 1,2-dichloroethane, then 10 g of isopropylphenyl sulphide [J. Chem. Soc. (1948), 1820]dissolved in 20 cm$^3$ of 1,2-dichloroethane, without the temperature exceeding +5° C. The whole is left to return to ambient temperature over one hour, then heated to reflux for one hour and a half. After evaporation to dryness, the residue is dissolved in 50 cm$^3$ of water, neutralized with sodium bicarbonate in solution at 10%, filtered and dried. 15 g of sodium salt is obtained which is treated with 150 cm$^3$ of methylene chloride and 11.55 g of phosphorus pentachloride, heating to reflux for 2 hours. After leaving to cool to ambient temperature, filtering and evaporating the solvent, 5 g of pure product is obtained.

EXAMPLE 18:

1-[4-(4-hexahydroazepin)phenylsulphonyl]-2-pyrrolidinone

Stage A: 4-(4-hexahydroazepinephenylsulphonylamino) butyric acid.

6 g of 4-hexahydroazepinebenzenesulphonyl chloride is added to a solution comprising 2.26 g of 4-aminobutyric acid and 2.6 g of sodium hydroxyde in solution in 60 cm$^3$ of water, then 60 cm$^3$ of tetrahydrofuran is added so as to obtain a solution. After agitation for 3 hours at ambient temperature, the solvent is evaporated off, the remainder is acidified with acetic acid, diluted with 100 cm$^3$ of water, and the precipitate is filtered off and dried. 3.8 g of expected product is obtained m.p.=133°-135° C. After crystallization from an ethanol-water mixture (1-1), m.p.=134°-135° C.

| Analysis: C$_{16}$H$_{24}$N$_2$O$_4$S: 340.454 | | | | | | |
|---|---|---|---|---|---|---|
| Calculated | C % | 56.45 | H % | 7.10 | N % | 8.23 |
| Found | | 54.55 | | 7.12 | | 8.22 |

Stage B:
1-[4-(4-hexahydroazepin)phenylsulphonyl]-2-pyrrolidinone.

A mixture comprising 3.5 g of product obtained in Stage A and 3.5 g of sodium acetate in 35 cm³ of acetic anhydride is taken to reflux for one hour. The mixture is cooled to ambient temperature and evaporated to dryness. The residue is taken up in 30 cm³ of water, filtered off and dried. 3 g of product is obtained which is chromatographed on silica (eluent: ethyl acetate). After crystallization from an isopropanol-water mixture (1-1), 2 g of product is obtained.
m.p.=155°-156° C.

| Analysis: C$_{16}$H$_{22}$N$_2$O$_3$S: 322.438 | | | | | | |
|---|---|---|---|---|---|---|
| Calculated | C % | 59.60 | H % | 6.88 | N % | 8.69 |
| Found | | 59.66 | | 6.94 | | 8.66 |

The 4-hexahydroazepinebenzenesulphonyl chloride used at the start of Example 18 was prepared as follows:

2.9 g of dioxane is added to a solution comprising 2.64 g of sulphuric anhydride in 78 cm³ of methylene chloride cooled to +5° C./+10° C., then at the same temperature 5.26 g of 1phenylhexahydroazepine in solution in 53 cm³ of methylene chloride is added. The mixture is allowed to return to ambient temperature, then heated to reflux for 2 hours. After cooling again to ambient temperature, 200 cm³ of ethyl ether is added, the precipitate is filtered off, washed with ether and dried and 7.2 g of acid is obtained, melting at 235° C. (decomp.). This acid is treated with 36 cm³ of phosphorus oxychloride, 36 cm³ of methylene chloride and 5.87 g of phosphorus pentachloride for 4 hours at ambient temperature. After evaporation to dryness, the residue is taken up with chloroform and with water; the organic phase is separated, dried on sodium sulphate, filtered and evaporated to dryness. 6.6 g of product is obtained which is used just as it is.
m.p.=85°-88° C.

EXAMPLE 19:
1-(4-piperazino)phenylsulphonyl]-2-pyrrolidinone

Stage A:
4-[4-(4-benzyloxycarbonylpiperazin-1-yl)phenylsulphonylamino]butyric acid.

10.5 g of 4-[(4-benzyloxycarbonyl)piperazin-1-yl]benzenesulphonyl chloride is added to a solution comprising 2.7 g of 4-amino butyric acid and 3.18 g of sodium hydroxyde in 50 cm³ of water, then 70 cm³ of tetrahydrofuran is added so as to obtain a solution. The solution is agitated for one hour at ambient temperature, the solvent is evaporated off, the remainder is acidified with acetic acid, then extracted with chloroform. The organic phase is dried on sodium sulphate, filtered off and evaporated to dryness. 8.2. g of expected product is obtained

Stage B:
1-[(4-piperazino)phenylsulphonyl]-2-pyrrolidinone.

8.2 g of product obtained in Stage A, 8.2. g of sodium acetate and 123 cm³ of acetic anhydride are heated to reflux for 30 minutes. The mixture is cooled to ambient temperature, evaporated to dryness, the residue is taken up with 100 cm³ of water, filtered and dried. 5.6 g of 1-[4-(4-benzyloxycarbonylpiperazin-1-yl)phenylsulphonyl]-2-pyrrolidinone is obtained. m.p. 153°-155° C. After recrystallization from an ethanol-acetone mixture (10-1), 3.7 g of product is obtained, melting at 158°-160° C. 7 g of product prepared as above and 1 g of palladium are put in suspension in 105 cm³ of dimethylacetamide, a few drops of triethylamine are added, then the whole is hydrogenated under ambient pressure (with 280 cm³ of hydrogen). The catalyst is filtered off, evaporated to dryness and 2 g of product is obtained which is dissolved in acetic acid and evaporated to dryness. The residue is taken up in isopropyl alcohol and 1.5 g of crystallized product is obtained.
m.p.=108° C.

| Analysis: C$_{14}$H$_{19}$N$_3$O$_3$S, CH$_3$COOH, 0.5 H$_2$O: 378.46 | | | | | | |
|---|---|---|---|---|---|---|
| Calculated | C % | 50.78 | H % | 6.39 | N % | 11.10 |
| Found | | 50.39 | | 6.15 | | 11.14 |

The 4-[(4-benzyloxycarbonyl)piperazin-1-yl]benzenesulphonyl chloride used at the start of Example 19 was prepared as follows:

Stage A: 4-carbobenzyloxyl 1-phenylpiperazine.

A solution of 4.4 g of benzyl chloroformate in toluene is added to a solution comprising 4.05 g of N-phenylpiperazine in 50 cm³ of benzene and 2.5 g of triethylamine, at a temperature between +5° C. and +10° C. The whole is allowed to return to ambient temperature and agitated for 2 hours. The triethylamine chloride is filtered off and evaporated to dryness. An oily residue is obtained which is solidified in n-hexane and 7.1 g of expected product is recovered.
m.p.=49°-51° C. After recrystallization from an ethyl ether-n-hexane mixture, m.p.=51°-52° C.

| Analysis: C$_{18}$H$_{20}$N$_2$O$_2$: 296.37 | | | | | | |
|---|---|---|---|---|---|---|
| Calculated | C % | 72.95 | H % | 6.80 | N % | 9.45 |
| Found | | 73.13 | | 6.79 | | 9.38 |

Stage B:
4-[(4-benzyloxycarbonyl)piperazin-1-yl]benzenesulphonyl chloride.

A solution comprising 3.04 g of sulphuric anhydride in 90 cm³ of methylene chloride is added to 11 g of product obtained in Stage A in solution in 100 cm³ of methylene chloride, then 3.6 g of dioxan is added, at a temperature between +5° C. and 10° C. The whole is allowed to return to ambient temperature, then heated to reflux for 2 hours, followed by cooling to ambient temperature, diluting with 300 cm³ of ethyl ether, filtering and drying. 13.7 g of product is obtained, melting at 210° C., which is treated with 100 cm³ of phosphorus oxychloride and 7.57 g of phosphorus pentachloride for 4 hours at ambient temperature. After evaporation to dryness, the residue is taken up with chloroform and with water, the organic phase is separated, dried on sodium sulphate, filtered off and evaporated to dryness. 10.6 g of product is obtained which is used just as it is.

EXAMPLES OF PHARMACEUTICAL COMPOSITIONS (a) Tablets were prepared corresponding to the following formula:

| Product of Example 1 | 10 mg |
|---|---|
| Excipient q.s. for a tablet completed at | 300 mg |

(Detail of excipient: lactose, wheat starch, treated starch, rice starch, magnesium stearate, talc.)

(b) Gelules were prepared corresponding to the following formula:

| Product of Example 1 | 20 mg |
|---|---|
| Excipient q.s. for a gelule completed at | 300 mg |

(Detail of excipient: talc, magnesium stearate, aerosil.)

BIOCHEMICAL AND PHARMACEUTICAL STUDIES (1) Bonding with the various cerebral receptors.

The results obtained by two significant examples of the invention are shown in the following table.

(a) Muscarine receptor 1

This is prepared from cortex removed from the brains of a male rat weighing 150 to 200 g, (Iffa Credo) pulverized with Polytron in a buffer Na/K 10 mM pH 7.4. After incubation (aliquots of 0.5 ml of homogenate) for 60 minutes at 25° C. in the presence of 0.25 nM of $^3$H pirenzepine, either alone, or with the product under test, or with an excess of pirenzepine at $10^{-5}$M (in order to determine the non-specific radioactivity fixed), the incubates are cooled and filtered.

The filtration is carried out on Whatman GF/C filters prewashed in a solution of polyethylene-imine at 0.05%. The filters are rinsed with 3×5 ml of phosphate Na/K buffer 10 mM pH 7.4, then measurements are made by liquid scintillation.

(b) Muscarine receptor 2

The preparation is made from the brains of a male rat weighing 150 to 200 g (Iffa Credo).

The brains are pulverized (Teflon-glass) in a 0.32M solution of sucrose. The homogenate is centrifuged for 10 minutes at 1000 g (0°–4° C.).

The supernatant obtained is recovered and centrifuged at 30,000 g for 15 minutes (0°–4° C.).

The deposit is put in suspension in a buffer Tris 50 mM pH 7.5 and the new homogenate is centrifuged again at 30,000 g for 15 minutes (0°–4° C.).

The deposits after elimination of the supernatant, can be used straight-away or kept for up to one month at −30° C.

For one experiment the deposits are first of all thawed out, if necessary, to ambient temperature and put in suspension, using a Dounce, in a buffer Tris 50 mM pH 7.5. Aliquots of 2 ml are incubated for 60 minutes at 25° C. in the presence of 0.3 nM of $^3$H quinuclidinyl benzylate either alone, or with the product under test, or with benzatropine at $10^{-5}$M in order to determine the non-specific radioactivity fixed.

At the end of the incubation the incubate tubes are cooled to 4° C. and filtered rapidly on Whatman GF/C filters. The filters are rinsed with 3×5 ml of buffer Tris 50 mM pH 7.5, then measurements are made by liquid scintillation [Henry I Yamamura, Solomon H. Snyder, Proc. Nat. Acad. Sc. (1974) 71 No. 5, 1725–1729).

The results are expressed in IC$_{50}$ (concentration necessary for inhibiting by 50% the specific radioactivity fixed.)

TABLE 1

| Compound of Example | Affinity for muscarine receptors M$_1$ and M$_2$ | |
|---|---|---|
| | /$^3$H/Pirenzepine | /$^3$H/Quinuclidinyl benzylate |
| 1 | 130 | 1300 |
| 2 | 98 | 1300 |

The compounds of examples 1 and 2 show a remarkable and useful affinity for the muscarine receptor, and mainly for the M$_1$ type receptor. By contrast the same compounds showed a negligible affinity (IC$_{50}$ 5000–10000) for the other receptors examined, among which there can be cited those of dopamine, of serotonine (5 HT$_1$ and 5 HT$_2$), of benzodiazepines, of GABA, adrenoreceptors (alpha 1, alpha 2, beta 1, beta 2) or even opiated receptors (mu, kappa).

(2) Interaction and affinity with various intestinal receptors

The interaction of the compounds with various receptors was evaluated on the isolated ileum of a guinea-pig according to the following method.

Segments of the ileum of guinea-pigs of 2.5–3 cm were washed and immediately suspended in a bath containing 10 ml of Tyrode's solution at 37° C. and aerated with a mixture of oxygen (95%) and carbon dioxide (5%). After a stabilization period of at least 30 minutes contractions were recorded, while the preparation was maintained under constant tension of 1 g, by means of a detector connected to a polygraph. The agonistic action was evaluated by leaving the compound in contact with the isolated tissue for a period necessary to show the maximum concentration; then it was washed with the Tyrode's solution. The following dose was added only after the preparation had returned to its base line. Arecoline was used as a reference product. The antagonist action was evaluated on the contractions induced by acetylcholine ($1\times10^{-6}$M), histamine ($1\times10^{-5}$M), serotonine ($1\times10^{-6}$M) and barium chloride ($2\times10^{-4}$M). Atropine diphenyldramine, methysergide and papaverine were used as reference products. The contact time before adding the agonist was one minute.

For each compound the does response curves are obtained with 4 to 6 different concentrations and 3 to 5 independent tests. The agonist activity is expressed by pD$_2$ (negative logarithm of the dose which produces 50% of the maximum effect). The antagonist activity is expressed by IC$_{50}$ (concentration inhibiting the maximum response by 50%). The results obtained with the compounds of examples 1 and 2 are shown in the following table:

TABLE 2

| Compound of Example | Antagonism with various agents (IC$_{50}$:M) | | | | Agonist Action (pD$_2$) |
|---|---|---|---|---|---|
| | Ach. | Istam. | Seroton. | BaCL$_2$ | |
| 1 | $6.4 \times 10^{-8}$ | $>10^{-4}$ | $>10^{-4}$ | $1.6 \times 10^{-5}$ | $<4$ |
| 2 | $6.2 \times 10^{-8}$ | $>10^{-4}$ | $>10^{-4}$ | $6.0 \times 10^{-6}$ | $<4$ |
| Atropine | $9.5 \times 10^{-9}$ | | | | |
| Diphenyl-dramine | | $8.3 \times 10^{-7}$ | | | |
| Methysergide | | | $1.1 \times 10^{-7}$ | | |
| Papaverine | | | | $4.5 \times 10^{-5}$ | |
| Arecoline | | | | | 6.68 |

The "in vitro" studies on the isolated ileum of guinea-pigs revealed that the compounds of the invention are powerful anti-muscarine agents. They antagonize the contractions induced by acetylcholine but not those induced by histamine and serotonine. These compounds showed an antagonist activity slightly lower (approx. 7 times) than that of atropine.

The remarkable antagonist action of the compounds of the invention was confirmed on the isolated colon of rats. In this test it was established whether the antagonist activity was of competitive or non-competitive type.

The following method was used: segments of the colon of rats of about 2.5 cm are washed and suspended in an insulated bath containing 10 ml of a solution of De Jalon having the following composition: (mM): NaCl 154; KCl 5.7; CaCl$_2$ 0.27; NaHCO$_3$ 5.9 and glucose 2.5. The temperature of the bath is maintained at 32° C. In these conditions, while maintaining the preparation under a tension of 1 g, the spontaneous activity of the colon is minimal. After a stabilization period of at least 30 minutes, the tension variations are recorded using an isometric transducer connected to a recorder. A series of tests was carried out to evaluate the antagonist activity in relation to the contractions induced by a maximum dose of acetylcholine. ($3 \times 10^{-6}$M).

The compounds are left in contact with the preparation for 3 minutes before adding acetylcholine.

Atropine was used as a reference product. For each compound the dose-response curves are obtained with 4 to 6 different concentrations and 3 to 5 independent tests.

The antagonist activity is expressed in IC$_{50}$ (concentration inhibiting the maximum response induced by acetylcholine by 50%).

In a second series of tests the acetylcholine is added to the bath in cumulative doses according to the van Rossum method (J. M. van Rossum, Arch, Int. Pharmacodyn. 143, 299, 1963). Having obtained two equal and consecutive dose-response curves with acetylcholine, a third dose-response curve is obtained in the presence of the compound (contact time of compound before acetylcholine=5 min.) Each compound was tested with 3-4 different concentrations The antagonist affinity and the type of antagonism (competitive, non-competitive) for the muscarine receptors was calculated according to Schild's method (H. D. Schild, Brit. J. Pharmacol. 2, 189, 1947).

TABLE 3

| Compound of Example | Isolated colon of rat | | |
|---|---|---|---|
| | IC$_{50}$ | pA$_2$ | "Slope" |
| 1 | $2.8 \times 10^{-7}$ | 7.77 | 0.89 |
| 2 | $1.6 \times 10^{-7}$ | 7.35 | 1.08 |
| Atropine | $2.7 \times 10^{-8}$ | 8.31 | 0.97 |

The two compounds of example 1 and 2, like atropine, gave a parallel displacement towards the right of the dose-response curve of acetyl-choline without reducing the maximum contraction.

The slope of the regression lines in the "Schild plot" corresponds to the theoretical value of 1 (tab. 3). According to this data and the values of pA$_2$ obtained (tab. 3) it can be concluded that the compounds of the invention are competitive antagonists for muscarine receptors, involved in the contractions of the colon of a rat induced by acetylcholine, and they show a power which is about 4 to 10 times inferior to that of atropine.

(3) "In vivo" anticholinergic action

The anticholinergic activity of the compounds was determined by evaluating the capacity to inhibit cholinomimetic effects induced by carbachol. Atropine sulphate was used as reference product.

CD$_1$ male mice are used weighing 25 to 30 g. They are divided into groups of 5 animals and treated by intraperitoneal route, in scaled doses, with the products or with 0.25% of Methocel for the controls. 10 animals are used for each dose. 30 minutes after the administration of the compounds, the mice are subcutaneously injected with 1 mg/kg of carbachol, dissolved in physiological serum.

Each animal was examined 30 minutes after the injection of carbachol to evaluate the presence of diarrhea, salivation and watering of the eyes; the body temperature was also measured using a thermocouple inserted 1.5 cm into the rectum.

The carbachol (1 mg/kg s.c.) induced diarrhea, salivation and watering of the eyes in all the control mice and a decrease in rectal temperature of about 2.5° C.

For each compound, there was determined, and recorded in the following table, the dose able to inhibit, in 50% of the animals, the appearance of peripheral cholinomimetic symptoms induced by carbachol, and to increase by 1° C. the hypothermic effect induced by the cholinergic agent.

TABLE 4

| Compound of Example | Dose mg/kg i.p. | | | |
|---|---|---|---|---|
| | Diarrhea | Salivation | Watering of Eyes | Body Temperature |
| 1 | 7 | 10 | >50 | 50 |
| 2 | 7 | >50 | >50 | >50 |
| 10 | 3 | 50 | >50 | >50 |
| 18 | 1 | 15 | 50 | 15 |

TABLE 4-continued

| Compound of Example | Dose mg/kg i.p. | | | |
| --- | --- | --- | --- | --- |
| | Diarrhea | Salivation | Watering of Eyes | Body Temperature |
| Atropine | 0.04 | 0.06 | 0.05 | 0.03 |

The results obtained show that, in contrast to atropine, the compounds of the examples, in particular those of examples 1, 2 and 10, exert "in vivo" a selective anticholinergic action on the intestinal musculature.

What is claimed is:

1. A therapeutic composition for the treatment of a patient suffering from muscle spasms, comprising an antispasmodically effective amount of a compound of Formula (I)

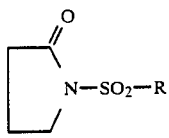
(I)

in which R represents the radical

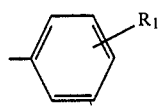

in which $R_1$ is in the 3 or 4 position on the phenyl nucleus, and represents a linear, branched or cyclic alkyl or alkenyl, containing up to 8 carbon atoms, or $R_1$ represents the radical

in which $R_2$ and $R_3$, identical or different, each represent a hydrogen atom, a linear alkyl or alkenyl, containing up to 8 carbon atoms, or $R_1$ represents $NO_2$, or $OR'$, $R'$ representing hydrogen, a linear, branched or cyclic alkyl containing up to 8 carbon atoms, phenyl or naphthyl, or $R_1$ is an $SR_4$ or $S(O)R_5$ radical, $R_4$ and $R_5$ representing a linear, branched or cyclic alkyl or alkenyl, containing up to 8 carbon atoms, or R represents naphythyl, optionally substituted by an $R_1$ radical, as defined above, and a pharmacologically acceptable carrier.

2. A therapeutic composition for the treatment of a patient suffering from muscle spasms, comprising an antispasmodically effective amount of a compound selected from the group consisting of 1-(4-tertbutylbenzene-sulphonyl)-2-pyrrolidinone, 1-[4-(diethylamino)-benzene-sulphonyl]-2-pyrrolidinone, 1-[4-(dimethylamino)benzene-sulphonyl]-2-pyrrolidinone, and 1-[4-(methylthio)benzene-sulphonyl]-2-pyrrolidinone, and a pharmacologically acceptable carrier.

3. A method of treating a patient suffering from muscle spasms comprising administering to the patient an antispasmodically effective amount of a compound of Formula (I)

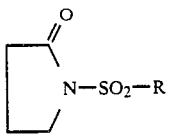
(I)

in which R represents the radical

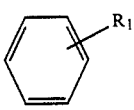

in which $R_1$ is in the 3 or 4 position on the phenyl nucleus, and represents a linear, branched or cyclic alkyl or alkenyl, containing up to 8 carbon atoms, or $R_1$ represents the radical

in which $R_2$ and $R_3$, identical or different, each represent a hydrogen atom, a linear alkyl or alkenyl, containing up to 8 carbon atoms, or $R_1$ represents $NO_2$, or $OR'$, $R'$ representing hydrogen, a linear, branched or cyclic alkyl containing up to 8 carbon atoms, phenyl or naphthyl, or $R_1$ is an $SR_4$ or $S(O)R_5$ radical, $R_4$ and $R_5$ representing a linear, branched or cyclic alkyl or alkenyl, containing up to 8 carbon atoms, or R represents naphthyl, optionally substituted by an $R_1$ radical, as defined above, and a pharmacologically acceptable carrier.

4. A method of treating a patient suffering from muscle spasms comprising administering to the patient an antispasmodically effective amount of a compound selected from the group consisting of 1-(4-tertbutylbenzene-sulphonyl)-2-pyrrolidinone, 1-[4-(diethylamino)-benzene-sulphonyl]-2-pyrrolidinone, 1-[4-(dimethylamino)benzene-sulphonyl]-2-pyrrolidinone, and 1-[4-(methylthio)benzene-sulphonyl]-2-pyrrolidinone.

* * * * *